United States Patent [19]

Ploog et al.

[11] Patent Number: 4,803,068
[45] Date of Patent: Feb. 7, 1989

[54] HAIR-TREATMENT PREPARATION FOR IMPROVED WET COMBABILITY

[75] Inventors: Uwe Ploog, Haan; Peter Busch, Erkrath-Unterbach; Klaus Thiele, Langenfeld; Horst Höffkes, Dusseldorf Hellerhof; Karl Giede, Hilden, all of Fed. Rep. of Germany

[73] Assignee: Henkel Kommanditgesellschaft auf Aktien, Duesseldorf, Fed. Rep. of Germany

[21] Appl. No.: 115,553

[22] Filed: Oct. 28, 1987

Related U.S. Application Data

[63] Continuation of Ser. No. 525,971, Aug. 24, 1983, abandoned.

[30] Foreign Application Priority Data

Jan. 24, 1983 [DE] Fed. Rep. of Germany ....... 3302210

[51] Int. Cl.$^4$ .................. A61K 7/075; A61K 7/08
[52] U.S. Cl. .................................. 424/70; 424/71
[58] Field of Search .................................. 424/70, 71; 252/DIG. 13, 174.16

[56] References Cited

U.S. PATENT DOCUMENTS 3,313,735 4/1967 McCune ........................... 252/548
3,400,176 9/1968 Quimby .......................... 252/174.16
3,671,644 6/1972 Irani et al. ....................... 252/106
4,105,573 8/1978 Jacobsen ......................... 252/99
4,126,572 11/1978 Tai .................................. 252/89 R

FOREIGN PATENT DOCUMENTS 1295138 5/1969 Fed. Rep. of Germany .
1393604 2/1965 France .

OTHER PUBLICATIONS

Shiseido Co., Ltd., cited in Chem. Abstracts, vol. 96:57590d, 1982.

Primary Examiner—Johnnie R. Brown
Assistant Examiner—Jacqueline M. Stone
Attorney, Agent, or Firm—Ernest G. Szoke; Wayne C. Jaeschke; Nelson Littell, Jr.

[57] ABSTRACT

Hair-treatment preparations containing as additive at least one surface-active phosphonic acid corresponding to general formula I, II or III below

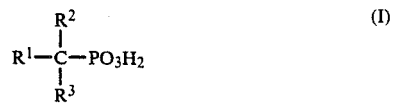

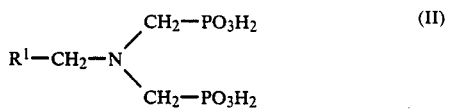

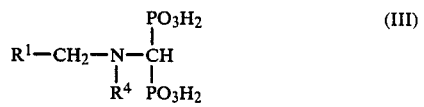

in which $R^1$ represents a $C_5$–$C_{21}$ alkyl, $R^2$ represents hydrogen or —$PO_3H_2$, and $R^3$ represents hydrogen, hydroxyl, or, if $R^2$ is —$PO_3H_2$, —$NH_2$, and $R^4$ represents hydrogen or a lower alkyl group containing from 1 to 4 carbon atoms, or a water-soluble salt thereof, improved the wet combability of hair and reduce its tendency to develop static charges. Octane-1-phosphonic acid, decane-1-phosphonic acid and dodecane-1-phosphonic acid or their salts are particularly effective. The phophonic acids are used in quantities of from 0.05 to 10% by weight, and preferably in quantities of from 0.1 to 2.0% by weight together with anionic tensides.

22 Claims, No Drawings

HAIR-TREATMENT PREPARATION FOR IMPROVED WET COMBABILITY

This application is a continuation of application Ser. No. 525,971, filed Aug. 24, 1983, now abandoned.

BACKGROUND OF THE INVENTION

This invention relates to cosmetic hair treatment preparations containing an additive to improve the wet-combability of hair.

After washing with shampoos based on synthetic surface-active compounds, hair is often in a cosmetically unsatisfactory condition. It feels dull and is difficult to comb in its wet state. After drying, the washed hair tends to develop a static charge, which makes combing difficult and prevents the combed hair from lying in the required manner.

It is known that conditioning preparations may be applied to the hair after washing or shampooing. The conditioning preparations in question are generally gel-like, liquid or emulsion-like lotions containing cation-active interface active compounds. It is also known that certain substances may be added to standard shampoos to obtain a certain conditioning effect when the hair is washed. Substances such as these are, for example, water-soluble proteins, protein degradation products or polycationic polymers, for example cationic cellulose derivatives. The disadvantages of cation-active surface-active compounds include their poor compatibility with anionic tensides and their often unsatisfactory compatibility with the mucous membrane.

Polycationic polymers, when present, do not counteract static charging of the dry hair and, in many cases, actually increase the tendency of the hair to develop a static charge. On the other hand, the strong adsorption of these cationic polymers onto the keratin fibers, particularly in the event of repeated application, results in an accumulation of the polymers on the hair which thus becomes "heavy" and loses elasticity, lay and body.

OBJECTS OF THE INVENTION

An object of the present invention is the development of hair-care preparations which contain additives improving the wet combability of hair and which are attended by few, if any, of the disadvantages referred to above.

Another object of the present invention is the development of an aqueous hair-treatment composition comprising at least one hair-treatment agent and an additive to improve the wet combability of hair wherein said hair-treatment composition contains an amount sufficient to improve the wet combability of hair of at least one surface-active phosphonic compound selected from the group consisting of (1) phosphonic acid compounds having the formula

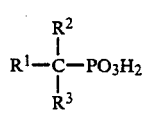

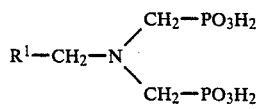

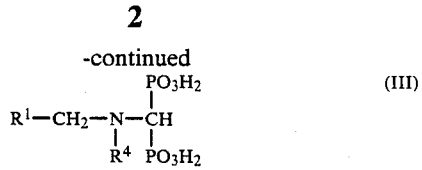

wherein $R^1$ is a $C_5$–$C_{21}$ alkyl, $R^2$ is a member selected from the group consisting of hydrogen and —$PO_3H_2$, $R^3$ is a member selected from the group consisting of hydrogen, hydroxy and, where $R^2$ is —$PO_3H_2$, —$NH_2$, and $R^4$ is a member selected from the group consisting of hydrogen and a $C_1$–$C_4$ lower alkyl, and (2) a water-soluble salt of said phosphonic acid compounds.

These and other objects of the invention will become more apparent as the description thereof proceeds.

DESCRIPTION OF THE INVENTION

We have now found that the wet combability of hair is distinctly improved in hair-treatment preparations containing as additive certain surface-active phosphonic acids containing a $C_6$–$C_{22}$ alkyl radical and from 1 to 2 phosphonic acid groups. These additives do not have any of the disadvantages of the known additives used for improving wet combability.

Accordingly, the present invention relates to hair-treatment preparations containing an additive to improve the wet combability of hair, characterized in that at least one surface-active phosphonic acid corresponding to general formula I, II or III below

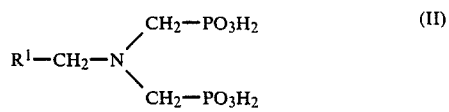

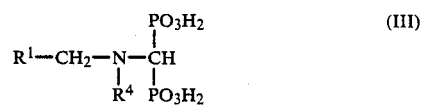

in which $R^1$ represents a $C_5$–$C_{21}$ alkyl, $R^2$ represents hydrogen or —$PO_3H_2$, $R^3$ represents hydrogen, hydroxyl or, if $R^2$ is —$PO_3H_2$, —$NH_2$ and $R^4$ represents hydrogen or a lower alkyl group containing from 1 to 4 carbon atoms, or a salt thereof, is present as the additive.

More particularly, the present invention relates to an aqueous hair-treatment composition comprising at least one hair-treatment agent and an additive to improve the wet combability of hair wherein said hair-treatment composition contains an amount sufficient to improve the wet combability of hair of at least one surface-active phosphonic compound selected from the group consisting of (1) phosphonic acid compounds having the formula

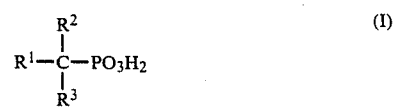

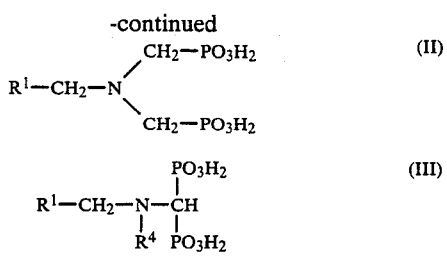

$$R^1-CH_2-N\begin{matrix}CH_2-PO_3H_2\\ \\ CH_2-PO_3H_2\end{matrix} \quad (II)$$

$$R^1-CH_2-N-\underset{PO_3H_2}{\overset{PO_3H_2}{CH}} \quad (III)$$
$$\qquad\quad\; |$$
$$\qquad\quad R^4$$

wherein $R^1$ is a $C_5$-$C_{21}$ alkyl, $R^2$ is a member selected from the group consisting of hydrogen and —$PO_3H_2$, $R^3$ is a member selected from the group consisting of hydrogen, hydroxy and, where $R^2$ is —$PO_3H_2$, —$NH_2$, and $R^4$ is a member selected from the group consisting of hydrogen and a $C_1$-$C_4$ lower alkyl, and (2) a water-soluble salt of said phosphonic acid compounds.

The surface-active phosphonic acids suitable for use as additives to the hair-treatment preparations according to the invention are known compounds or may be obtained by methods known from the literature. They include, for example, the alkane-1-phosphonic acids containing from 6 to 22 carbon atoms which may be obtained in accordance with U.S. Pat. No. 2,957,931 by the radical addition of esters of phosphorous acid onto olefins, followed by hydrolysis.

Alkane-1,1-diphosphonic acids may be obtained, for example, by alkylating methane diphosphonic acid using the process described by G. M. Kosolapoff in J. Am. Chem. Soc. 75 (1953), pages 1500–1501, for pentane-1,1-diphosphonic acid.

1-hydroxyalkane-1-phosphonic acids can be obtained, for example, by the method described by W. Fossek in Monatschefte fur Chemie, Vol. 7, (1886), pages 20 to 39, in which aldehydes are reacted with $PCl_3$.

1-hydroxyalkane-1,1-diphosphonic acids may be obtained from carboxylic acids, water and $PCl_3$ by the process described by B. Blasser et al. in Zeitschrift fur anorganische und allgemeine Chemie, Vol. 381 (1971), pages 247 to 259.

1-aminoalkane-1,1-diphosphonic acids may be obtained by a process described by W. Ploger et al. Zeitschrift fur anorganische und allgemeine Chemie, Vol. 389 (1972), pages 119 to 128.

This process may also be used for obtaining the compounds corresponding to general formula III, the N-monosubstituted and N,N-disubstituted aminomethane diphosphonic acids.

The compounds corresponding to general formula II may be obtained from the corresponding alkylamine, formaldehyde and phosphorous acid by the process known from DE-AS No. 12 14 229.

Particularly suitable surface-active phosphonic acids are the compounds corresponding to general formulae I and II in which $R^1$ is a linear $C_7$-$C_{13}$ alkyl group and $R^2$ and $R^3$ represent hydrogen. The most suitable phosphonic acids are octane-1-phosphonic acid, decane-1-phosphonic acid and dodecane-1-phosphonic acid. The compounds mentioned may be added to the hair-treatment preparations in the form of the free acids or as salts, preferably as water-soluble salts, for example as alkali metal or ammonium salts. The hair-treatment preparations according to the invention improve the wet combability of hair by virtue of the addition thereto of surface-active phosphonic acids or their salts. At the same time, the surface-active phosphonic acids or their salts reduce the tendency of the hair to develop static charges, but do not lead to an accumulation of the conditioning components on the surface of the hair with the familiar, undesirable effects which that involves.

Their stability in alkaline formulations and their resistance to oxidizing and reducing formulation ingredients distinguishes them from most additives used for improving wet combability. Accordingly, these additives may also be incorporated in hair dyes, hair bleaches and permanent-wave preparations.

The surface-active phosphonic acids develop their effect even in very low concentrations. The hair-treatment preparations according to the invention may contain from 0.05 to 10% by weight of these additives, although in most cases an addition of from 0.1 to 2.0% by weight of the surface-active phosphonic acids is sufficient to obtain a satisfactory effect.

Another advantage of the surface-active phosphonic acids and their salts is their outstanding compatibility with anionic tensides of the type commonly used for numerous hair-cosmetic preparations, for example shampoos, hair dyes and hair bleaches.

The anionic tensides used in the hair treatment preparations according to the invention are alkyl sulfates and/or alkyl polyglycol ether sulfates containing from 10 to 18 carbon atoms in the alkyl group and up to 12 polyglycol ether groups, preferably polyethyleneglycol ether groups, and/or alkyl polyglycol ether sulfosuccinic acid monoesters containing from 10 to 16 carbon atoms in the alkyl group and from 2 to 6 glycol ether groups, preferably ethyleneglycol ether groups. Other suitable anionic tensides for the hair-treatment preparations according to the invention are primary and secondary linear alkane sulfonates containing from 10 to 18 carbon atoms, alkene sulfonates and hydroxyalkane sulfonates of the type obtained in the sulfonation of olefins containing from 10 to 18 carbon atoms, higher fatty acid alkylol amide and higher fatty acid alkylol amide polyethyleneglycol ether sulfates, sulfated higher fatty acid monoglycerides, alkyl polyglycol ether carboxylates containing from 8 to 18 carbon atoms in the alkyl chain and from 2 to 6 ethyleneglycol ether groups, acyl sarcosines, acyl taurides and acyl isothionates containing from 8 to 18 carbon atoms in the acyl group.

The anionic tensides mentioned may be present in the form of their alkali metal, ammonium or alkanolammonium salts; the alkyl sulfates and alkyl polyglycol ether sulfates may even be present in the form of their magnesium salts. They are normally present in quantities of from 2 to 50% by weight, based on the hair treatment preparation as a whole.

A particularly pronounced reduction in the resistance to combing was observed in the case of hair treatment preparations which contain the surface-active phosphonic acids and, as anionic tensides, a mixture of an alkyl polyglycol ether sulfate alkali metal salt containing from 10 to 16 carbon atoms in the alkyl group and from 2 to 4 ethyleneglycol ether groups and an alkyl polyglycol ether sulfosuccinic acid monoester alkali metal salt containing from 10 to 16 carbon atoms in the alkyl group and from 2 to 4 ethyleneglycol ether groups.

The hair treatment preparations according to the invention may also contain other surface-active substances, for example nonionic, zwitterionic and amphoteric tensides and/or standard auxiliaries and additives, such as fatty alcohols, water-soluble nonionic or anionic polymers, for example cellulose ethers, alkyleneglycols, inorganic salts, buffer substances, preservatives, dyes, fragrances, active hair-cosmetic ingredients, such as for example antidandruff agents, sebostatics, vitamins, herbal extracts and also reducing agents for shaping the hair, oxidizing agents for setting shaped hair or for bleaching hair and oxidation dye precursors for dyeing the hair. Using the auxiliaries and additives mentioned, the hair-treatment preparations according to the invention may be made up in the form of shampoos, hair aftertreatment preparations, hair cure preparations, permanent-wave preparations, permanent-wave setting preparations, hair dyes or hair bleaches.

The following Examples are intended to illustrate the invention without limiting it in any way.

EXAMPLES

1. Wet-combability test WC [%]

The effect of additions of surface-active phosphonic acids and their salts on the wet-combability of hair was tested by the following method:

Strands of brown, european hair approximately 11 cm long and weighing 0.8 gram, which had been subjected to a single bleaching and cold-wave treatment under controlled conditions, were treated for 5 minutes at 30° C. with a solution of 2.0% by weight of the surface-active phosphonic acid in an aqueous tensides solution and then thoroughly rinsed in luke-warm water (30° C.). Excess water was stripped off. The combining resistance was then measured, being the force required to pull a comb through a strand of hair. To reduce any errors, the measurement was carried out 15 times with each of the products to be tested and the average value of the work integrals determined. The measurement was carried out in a Zwick type 1402 tensile testing machine (Zwick, Einsingen uber Ulm/Donau).

The average work integral was based on the work integral obtained by treatment with the particular tenside solution in the absence of active substance (blank value) and thus showed the improvement (or deterioration) in wet combability:

$$WC\ [\%] = \frac{\text{work integral active substance}}{\text{work integral blank value}} \cdot 100$$

Accordingly, values below 100% indicate an improvement and values over 100% a deterioration in wet combability.

The results obtained with surface-active phosphonates used in accordance with the invention in hair-treatment preparations are shown in Table I.

TABLE I

| Surface-active phosphonate 2% by weight | Tenside | % by weight of tenside in $H_2O$ | WC [%] |
|---|---|---|---|
| Hexane-1-phosphonic acid | $C_{12-14}$ fatty alcohol + 2EO-sulfate, Na salt | 14 | 78% |
| Octane-1-phosphonic acid | $C_{12-14}$ fatty alcohol + 2EO-sulfate, Na salt | 14 | 16% |
| Decane-1-phosphonic acid | $C_{12-14}$ fatty alcohol + 2EO-sulfate, Na salt | 14 | 20% |
| Octadecane-1-phosphonic acid | $C_{12-14}$ fatty alcohol + 2EO-sulfate, Na salt | 14 | 48% |
| Dodecylamino-di(methylene)-phosphonic acid | $C_{12-14}$ fatty alcohol + 2EO-sulfate, Na salt | 14 | 30% |
| 1-aminodecane-1, 1-diphosphonic acid | $C_{12-14}$ fatty alcohol + 2EO-sulfate, Na salt | 14 | 66% |
| Octane-1-phosphonic acid | lauryl sulfate triethanolammonium salt | 14 | 31% |
| Octane-1-phosphonic acid | $C_{12-14}$ fatty alcohol + 2EO-sulfate, Na salt | 11 | 41% |
|  | N—hydroxyethyl-N—coconut-alkylamido-ethyl glycine | 3 |  |
| Octane-1-phosphonic acid | $C_{12-14}$ fatty alcohol + 2EO-sulfate, Na salt | 11 | 56% |
|  | coconut alkylamidopropy-dimethyl glycine | 3 |  |
| Octane-1-phosphonic acid | $C_{12-14}$ fatty alcohol + 2EO-sulfate, Na salt | 11 | 9% |
|  | $C_{12-14}$ fatty alcohol + 2EO sulfosuccinic acid monoester, Na salt | 3 |  |
| 1-hydroxyoctane-1,1-diphosphonic acid | $C_{12-14}$ fatty alcohol + 2EO-sulfate, Na salt | 14 | 64% |

2. Formulations for hair-care preparations according to the invention

2.1 Shampoos

2.1.1 Toning shampoo with a mild conditioning effect

| | |
|---|---|
| $C_{12-14}$ fatty alcohol + 2EO-sulfate, Na salt (28%) (Texapon ® N25) | 40% by weight |
| coconut alkylamido-propyl-dimethyl glycine (30%) (Dehyton ® K) | 10% by weight |
| decane-1-phosphonic acid, Na salt | 0.1% by weight |
| water, colorants, fragrances, preservatives | ad 100% by weight |

2.1.2 Shampoo for lifeless hair

| | |
|---|---|
| $C_{12-14}$ fatty alcohol + 2EO-sulfate, Na salt (28%) | 40% by weight |
| $C_{12-14}$ fatty alcohol + 2E0 sulfo-succinic acid monoester, Na salt (30%) | 10% by weight |
| octane-1-phosphonic acid, Na salt | 1.0% by weight |
| water, colorants, fragrances, preservatives | ad 100% by weight |

The hair washed with these shampoos shows good wet-combability and does not develop an electrostatic charge when combed after drying.

2.2 Hair aftertreatment preparations

2.2.1 Acidic, rinsable hair gel

| | |
|---|---|
| octane-1-phosphonic acid | 5.0% by weight |
| hydroxyethylcellulose | 0.8% by weight |
| water, fragrances, colorants | ad 100% by weight |

| | | |
|---|---|---|
| -continued | | |
| 2.2 Hair aftertreatment preparations | | |
| preservatives | | |
| 2.2.2 Emulsion-like, acidic hair rinse | | |
| cetyl-stearyl alcohol | 1.5% by weight | |
| stearic acid mono-di-glyceride | 1.5% by weight | |
| cetyl-stearyl alcohol poly(20EO)-glycol ether | 3.0% by weight | |
| nonylphenylpoly(6.5EO) glycol ether | 2.0% by weight | |
| octane-1-phosphonic acid | 2.0% by weight | |
| water, colorants, fragrances preservatives | ad 100% by weight | |

The rinsing preparations impart, to the wet and dried hair, better combability and a pleasant feel. The hair does not develop an electrostatic charge when combed with a hard rubber comb.

The preceeding specific embodiments are illustrative of the practice of the invention. It is to be understood however that other expedients known to those skilled in the art or disclosed herein, may be employed without departing from the spirit of the invention or the scope of the appended claims.

We claim:

1. A process for improving the wet combability of hair which comprises applying to said hair an aqueous hair-treatment composition comprising at least one hair-treatment agent and an additive to improve the wet combability of hair wherein said aqueous hair-treatment composition contains an amount sufficient to improve the wet combability of hair of at least one surface-active phosphonic compound selected from the group consisting of:
   (1) phosphonic acid compounds having the formula $$R^1-CH_2-PO_3H_2$$

wherein $R^1$ is a linear $C_7-C_{13}$ alkyl, and
   (2) a water-soluble salt of said phosphonic acid compounds as said additive to improve the wet combability of hair.

2. The process of claim 1, wherein said at least one surface-active phosphonic acid is octane-1-phosphonic acid, decane-1-phosphonic acid or dodecane-1-phosphonic acid or a salt thereof.

3. The process of claim 1 wherein said aqueous hair-treatment composition is in the form of a shampoo, wherein said at least one surface-active phosphonic acid or their water-soluble salts are present in an amount of from 0.05% to 10% by weight and said at least one hair-treatment agent comprises anionic tensides present in an amount of from 2% to 50% by weight, based on the preparation as a whole.

4. The process of claim 3, wherein said surface-active phosphonic acids or their water-soluble salts are present in an amount of from 0.1% to 2.0% by weight, and a mixture of an alkyl polyglycol ether sulfate, alkali metal salt, containing from 10 to 16 carbon atoms in the alkyl group and from 2 to 4 ethyleneglycol ether groups and an alkyl polyglycolether sulfosuccinic acid monoester, alkali metal salt, containing from 10 to 16 carbon atoms in the alkyl group and from 2 to 4 ethyleneglycol ether groups is present as anionic tenside in a quantity of from 2 to 50% by weight, based on the hait treatment preparation as a whole.

5. In a process for improving the wet combability of hair comprising applying to said hair an aqueous shampoo comprising from 2% to 50% by weight of at least one anionic tenside and an amount sufficient to improve wet combability of an additive, the improvement consisting essentially of employing from about 0.05% to 10% by weight of at least one phosphonic acid having the formula $$R^1-CH_2-PO_3H_2$$

in which $R^1$ represents a linear $C_7-C_{13}$ alkyl, or an alkali metal salt thereof, as said additive.

6. The process of claim 5 wherein said at least one phosphonic acid is octane-1-phosphonic acid, decane-1-phosphonic acid or dodecane-1-phosphonic acid or an alkali metal salt thereof.

7. The process of claim 3 wherein said anionic tensides are members selected from the group consisting of alkyl sulfates having from 10 to 18 carbon atoms in the alkyl group, alkyl polyglycol ether sulfates having from 10 to 18 carbons in the alkyl and up to 12 polyethyleneglycol ether groups, alkyl polyglycol ether sulfosuccinic acid monoesters having from 10 to 16 carbon atoms in the alkyl and from 2 to 6 ethyleneglycol ether groups, and mixtures thereof.

8. The process of claim 1 wherein said at least one hair-treatment agent is a member selected from the group consisting of anionic tensides, nonionic tensides, zwitterionic tensides, amphoteric tensides, fatty alcohols, water-soluble nonionic or anionic polymers, alkyleneglycols, inorganic salts, buffer substances, preservatives, dyes, fragrances, antidandruff agents, sebostatics, vitamins, herbal extracts, reducing agents for shaping the hair, oxidizing agent for setting shaped hair or for bleaching hair, and oxidation dye precursors for dyeing the hair.

9. The process of claim 1 wherein said phosphonic compound is n-octane-1-phosphonic acid.

10. The process of claim 1 wherein said phosphonic compound is n-decane-1-phosphonic acid.

11. The process of claim 1 wherein said phosphonic compound is n-dodecane-1-phosphonic acid.

12. The process of claim 1 wherein said phosphonic compound is n-tetradecane-1-phosphonic acid.

13. An aqueous hair-treatment composition comprising at least one hair-treatment agent and an additive to improve the wet combability of hair wherein said aqueous hair-treatment composition contains an amount sufficient to improve the wet combability of hair of at least one surface-active phosphonic compound selected from the group consisting of:
   (1) phosphonic acid compounds having the formula:

$$R^1-CH_2-PO_3H_2$$

wherein $R^1$ is a linear $C_7-C_{13}$ alkyl, and
   (2) a water-soluble salt of said phosphonic acid compounds as said additive to improve the wet combability of hair, such composition further characterized as being free of detergent builder salts.

14. The hair-treatment composition of claim 13, wherein said at least one surface-active phosphonic acid is octane-1-phosphonic acid, decane-1-phosphonic acid or dodecane-1-phosphonic acid or a salt thereof.

15. The hair-treatment composition of claim 13 in the form of a shampoo, wherein said at least one surface-active phosphonic acid or their water-soluble salts are present in an amount of from 0.05% to 10% by weight and said at least one hair-treatment agent comprises anionic tensides present in an amount of from 2% to 50% by weight, based on the preparation as a whole.

16. The hair-treatment composition of claim 15, wherein said surface-active phosphonic acids or their water-soluble salts are present in an amount of from 0.1% to 2.0% by weight, and a mixture of an alkyl polyglycol ether sulfate, alkali metal salt, containing from 10 to 16 carbon atoms in the alkyl group and from 2 to 4 ethyleneglycol ether groups and an alkyl polyglycolether sulfosuccinic acid monoester, alkali metal salt, containing from 10 to 16 carbon atoms in the alkyl group and from 2 to 4 ethyleneglycol ether groups is present as anionic tenside in a quantity of from 2 to 50% by weight, based on the hair treatment preparation as a whole.

17. The aqueous hair-treatment composition of claim 15 wherein said anionic tensides are members selected from the group consisting of alkyl sulfates having from 10 to 18 carbon atoms in the alkyl group, alkyl polyglycol ether sulfates having from 10 to 18 carbons in the alkyl and up to 12 polyethyleneglycol ether groups, alkyl polyglycol ether sulfosuccinic acid monoesters having from 10 to 16 carbon atoms in the alkyl and from 2 to 6 ethyleneglycol ether groups, and mixtures thereof.

18. The aqueous hair-treatment composition of claim 13 wherein said at least one hair-treatment agent is a member selected from the group consisting of anionic tensides, nonionic tensides, zwitterionic tensides, amphoteric tensides, fatty alcohols, water-soluble nonionic or anionic polymers, alkyleneglycols, inorganic salts, buffer substances, preservatives, dyes, fragrances, antidandruff agents, sebostatics, vitamins, herbal extracts, reducing agents for shaping the hair, oxidizing agents for setting shaped hair or for bleaching hair, and oxidation dye precursors for dyeing the hair.

19. The aqueous hair-treatment composition of claim 13 wherein said phosphonic acid compound is n-octane-1-phosphonic acid.

20. The aqueous hair-treatment composition of claim 13 wherein said phosphonic acid compound is n-decane-1-phosphonic acid.

21. The aqueous hair-treatment composition of claim 13 wherein said phosphonic acid compound is n-dodecane-1-phosphonic acid.

22. The aqueous hair-treatment composition of claim 13 wherein said phosphonic acid compound is n-tetradecane-1-phosphonic acid.

* * * * *